United States Patent [19]
Mastri et al.

[11] Patent Number: 6,024,750
[45] Date of Patent: Feb. 15, 2000

[54] ULTRASONIC CURVED BLADE

[75] Inventors: Dominick L. Mastri, Bridgeport, Conn.; Corbett W. Stone, San Diego, Calif.

[73] Assignee: United States Surgical, Norwalk, Conn.

[21] Appl. No.: 08/911,205

[22] Filed: Aug. 14, 1997

[51] Int. Cl.[7] .................................................. A61M 17/32
[52] U.S. Cl. .......................................... 606/169; 606/174
[58] Field of Search .................................... 606/1, 39–52, 606/167, 174, 205–210; 604/22; 601/2

[56] References Cited

U.S. PATENT DOCUMENTS

| | | |
|---|---|---|
| 2,002,594 | 5/1935 | Wappler et al. . |
| 2,011,169 | 8/1935 | Wappler . |
| 2,714,890 | 8/1955 | Vang . |
| 2,874,470 | 2/1959 | Richards . |
| 3,086,288 | 4/1963 | Balamuth et al. . |
| 3,427,480 | 2/1969 | Robinson . |
| 3,526,219 | 9/1970 | Balamuth . |
| 3,636,943 | 1/1972 | Balamuth . |
| 3,752,161 | 8/1973 | Bent . |
| 3,792,701 | 2/1974 | Kloz et al. . |
| 3,862,630 | 1/1975 | Balamuth . |
| 3,899,829 | 8/1975 | Storm et al. . |
| 3,930,173 | 12/1975 | Banko . |
| 4,428,748 | 1/1984 | Peyman et al. . |
| 4,672,965 | 6/1987 | Baum . |
| 4,682,597 | 7/1987 | Myers . |
| 5,026,387 | 6/1991 | Thomas . |
| 5,047,043 | 9/1991 | Kubota et al. . |
| 5,057,098 | 10/1991 | Zelman . |
| 5,059,210 | 10/1991 | Clark et al. . |
| 5,167,725 | 12/1992 | Clark et al. . |
| 5,180,363 | 1/1993 | Idemoto et al. . |
| 5,188,102 | 2/1993 | Idemoto et al. . |
| 5,190,541 | 3/1993 | Abele et al. . |
| 5,201,759 | 4/1993 | Ferzli . |
| 5,217,460 | 6/1993 | Knoepfler . |
| 5,222,937 | 6/1993 | Kagawa . |
| 5,263,957 | 11/1993 | Davison . |
| 5,267,998 | 12/1993 | Hagen . |
| 5,322,055 | 6/1994 | Davison et al. . |

(List continued on next page.)

FOREIGN PATENT DOCUMENTS

| | | |
|---|---|---|
| 0 394 583 | 10/1990 | European Pat. Off. . |
| 2 032 501 | 1/1972 | Germany . |
| 1 232 948 | 9/1989 | Japan . |
| 1-232949 | 9/1989 | Japan . |
| 63-061609 | 5/1993 | Japan . |
| 1155256 | 5/1985 | U.S.S.R. . |
| WO 86/02257 | 4/1986 | WIPO . |
| WO 94/20025 | 9/1994 | WIPO . |

*Primary Examiner*—Michael Buiz
*Assistant Examiner*—William W. Lewis

[57] ABSTRACT

An ultrasonic dissection and coagulation system for surgical use is provided. The system includes an ultrasonic instrument, a control module, and a remote actuator. The ultrasonic instrument has a housing and an elongated body portion extending from the housing. An ultrasonic transducer supported within the housing is operatively connected to a cutting jaw by a vibration coupler. The vibration coupler conducts high frequency vibration from the ultrasonic transducer to the cutting jaw. The cutting jaw has a blade surface which is curved downwardly and outwardly in the distal direction with respect to the longitudinal axis of the elongated body portion along its length such that an angle defined by a line drawn tangent to the blade surface and the longitudinal axis of the elongated body portion varies between 5 degrees and 75 degrees. A clamp member having a tissue contact surface is positioned adjacent to the cutting jaw and is movable from an open position in which the tissue contact surface is spaced form the blade surface to a clamped position in which the tissue contact surface is in close juxtaposed alignment with the blade surface to clamp tissue therebetween. The clamp member and the curved cutting jaw combine to enhance contact between tissue and the blade surface of the cutting jaw during cutting. Further, the continuously varying angle of the blade surface with respect to the longitudinal axis of the elongated body portion facilitates selective user control over the application of force on tissue during a cutting or dissecting procedure.

20 Claims, 15 Drawing Sheets

U.S. PATENT DOCUMENTS

| | | |
|---|---|---|
| 5,334,183 | 8/1994 | Wuchinich . |
| 5,352,222 | 10/1994 | Rydell . |
| 5,389,104 | 2/1995 | Hahnen et al. . |
| 5,441,512 | 8/1995 | Muller . |
| 5,562,693 | 10/1996 | Devlin et al. . |
| 5,776,155 | 7/1998 | Beaupre et al. . |
| 5,800,448 | 9/1998 | Banko . |
| 5,810,859 | 9/1998 | DiMatteo et al. . |
| B1 5,322,055 | 10/1997 | Davison et al. . |

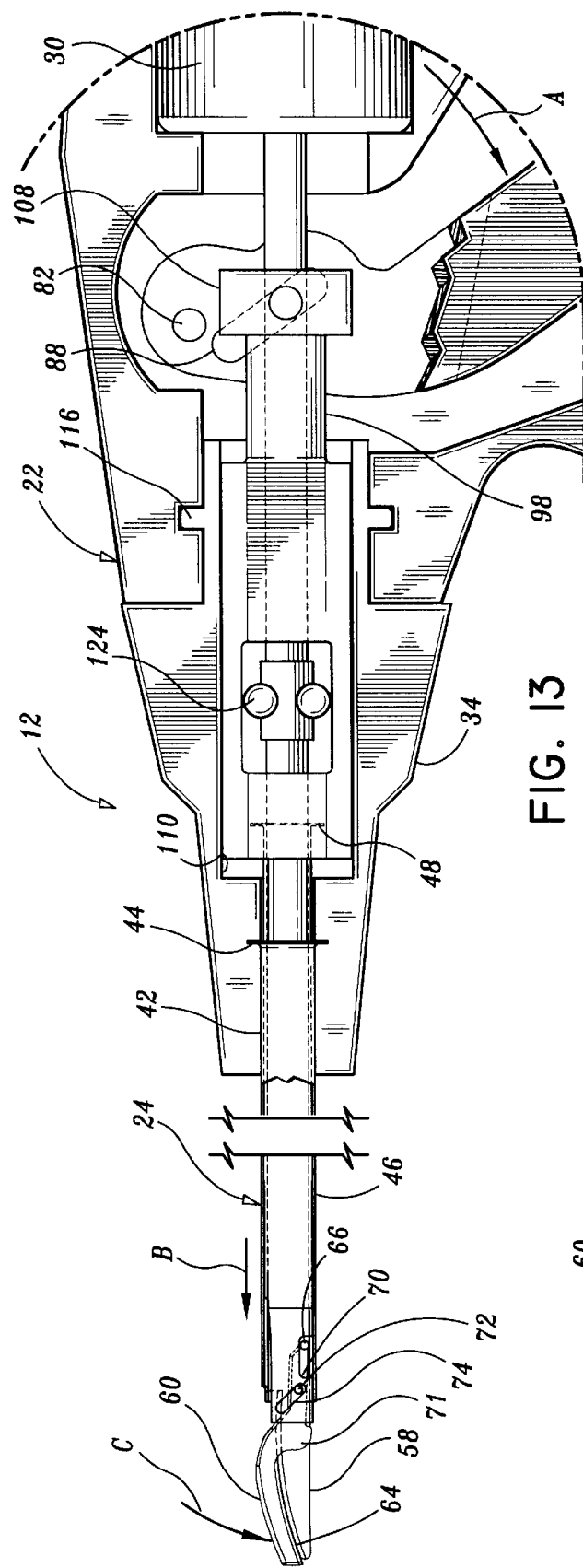
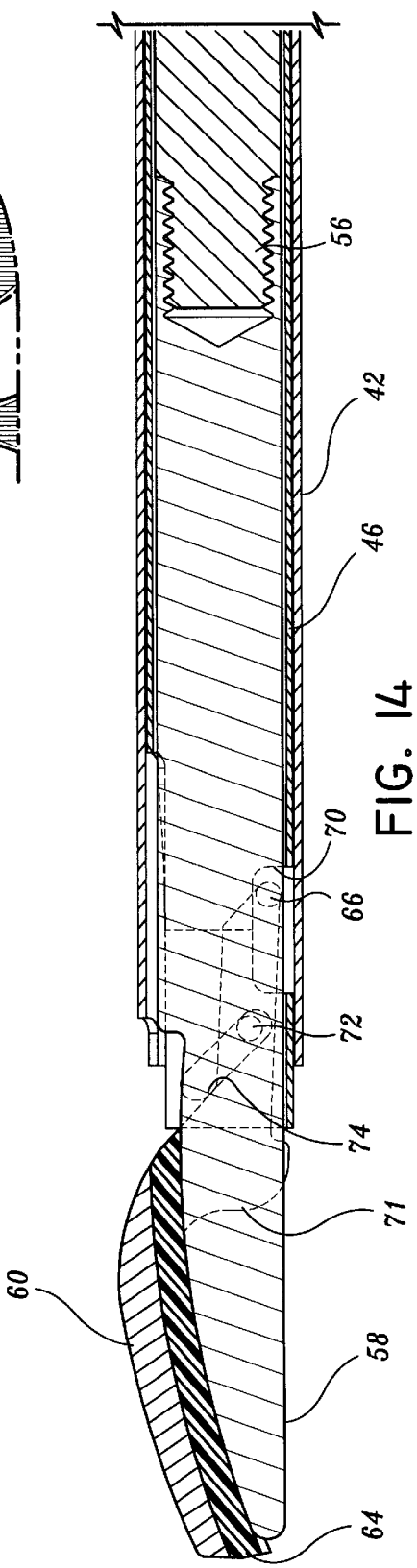
FIG. 13
FIG. 14

ULTRASONIC CURVED BLADE

BACKGROUND

1. Technical Field

The present disclosure relates to an ultrasonic dissection and coagulation system for surgical use. More specifically, the present disclosure relates to an ultrasonic instrument including a curved blade and a clamp member particularly suited for performing dissection and coagulation of tissue.

2. Background of Related Art

Ultrasonic instruments for surgical use and the benefits associated therewith are well known. For example, the use of an ultrasonic generator in conjunction with a surgical scalpel facilitates faster and easier cutting of organic tissue and accelerates blood vessel clotting in the area of the cut, i.e., accelerated coagulation. Improved cutting results from increased body tissue to scalpel contact caused by the high frequency of vibration of the scalpel blade with respect to body tissue. Improved coagulation results from heat generated by contact between the scalpel blade and the body tissue as the scalpel blade is vibrated at a high frequency. Thus, in order to reap the advantages associated with ultrasonic energy, good blade to tissue contact is important.

U.S. Pat. No. 3,862,630 ("Balamuth") discloses an ultrasonic system including an ultrasonic motor, a tool member having a working surface oriented normal to the direction of mechanical vibration generated by the ultrasonic motor, and a clamp member extending parallel to the tool member for compressing tissue against the tool member. U.S. Pat. No,. 5,322,055 ("Davison") discloses an ultrasonic surgical instrument adapted for endoscopic use having a blade and a clamp movable in relation to the blade to capture tissue therebetween. The blade and the clamp define a clamping region having a plane which is parallel to the longitudinal axis of the surgical instrument. During an endoscopic procedure, movement of the instrument is limited to movement along an axis parallel to the plane of the clamping region. Thus, no additional blade force is imposed on the body tissue as a result of movement of the instrument.

Accordingly, a need exists for an improved ultrasonic surgical instrument which is easy to use and provides fast and easy cutting and improved coagulation.

SUMMARY

In accordance with the present disclosure, an ultrasonic system for dissection and coagulation of tissue is provided. The system includes an ultrasonic instrument, a control module, and a remote actuator. The ultrasonic instrument has a housing and an elongated body portion extending from the housing. An ultrasonic transducer supported within the housing is operatively connected to a cutting jaw by a vibration coupler. The vibration coupler conducts high frequency vibration from the ultrasonic transducer to the cutting jaw. The cutting jaw has a blade surface which is curved outwardly and downwardly along its surface and thus, curved with respect to the axis of vibration. The curved blade surface is preferably configured such that the angle defined between a line tangent to the blade surface and the longitudinal axis of the elongated body portion varies from about 5 degrees to about 45 degrees along the length of the blade surface. A clamp member having a tissue contact surface is positioned adjacent to the cutting jaw and is movable from an open position in which the tissue contact surface is spaced from the blade surface to a clamped position in which the tissue contact surface is in close juxtaposed alignment with the blade surface to clamp tissue therebetween. The clamp member and the angled blade combine to enhance contact between tissue and the blade surface of the blade member.

BRIEF DESCRIPTION OF THE DRAWINGS

FIG. 13 is an enlarged view of the indicated area of detail of FIG. 12 illustrating the clamp in the closed position;

FIG. 14 is a side cross-sectional view of the distal end of the elongated body portion of the ultrasonic instrument of FIG. 1 in the clamped position;

DETAILED DESCRIPTION OF THE PREFERRED EMBODIMENTS

Figure 1:
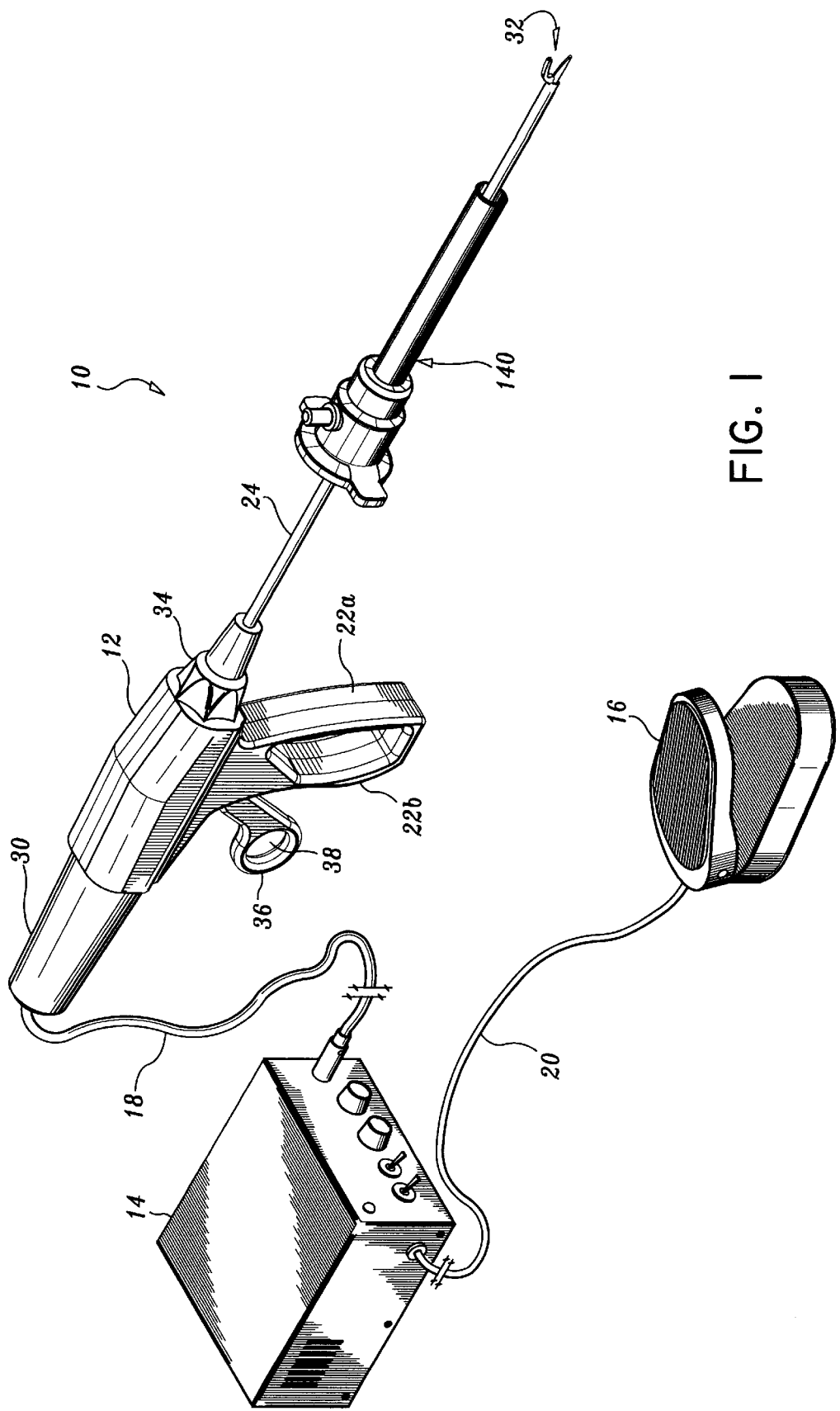
FIG. 1 is a perspective view of the ultrasonic dissection and coagulation system with the ultrasonic instrument inserted partially through a cannula.

Preferred embodiments of the presently disclosed ultrasonic dissection and coagulation system will now be described in detail with reference to the drawings, in which like reference numerals designate identical or corresponding elements in each of the several views.

FIG. 1 illustrates the ultrasonic dissection and coagulation system shown generally as 10. Briefly, dissection and coagulation system 10 includes ultrasonic instrument 12, control module 14, and remote actuator 16. Control module 14 is operatively connected to ultrasonic instrument 12 by electrically conductive cable 18 and functions to control the power and frequency of current supplied to ultrasonic instrument 12. Any suitable controller capable of delivering power to ultrasonic instrument 12 can be used. Control module 14 does not form part of the invention and will not be further discussed herein. Remote actuator 16, e.g., pedal actuator, is operatively connected to control module 14 by electrically conductive cable 20 and can be actuated to initiate the supply of power to ultrasonic instrument 12 via control module 14 to effect vibratory motion of ultrasonic instrument 12 to cut and coagulate tissue.

Figure 2:
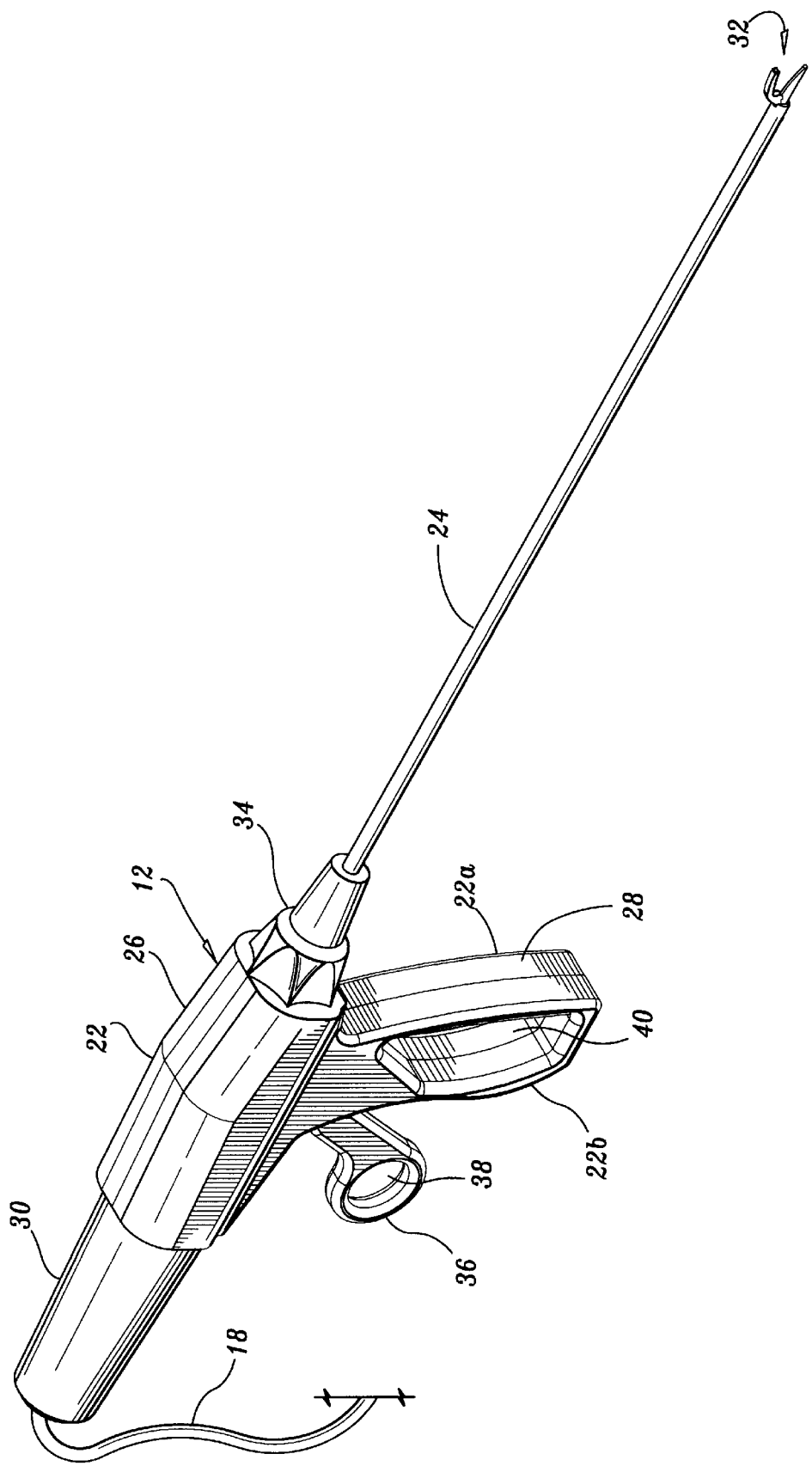
FIG. 2 is a perspective view of the ultrasonic instrument of FIG. 1.

As illustrated in FIG. 2, ultrasonic instrument 12 includes housing 22 and elongated body portion 24 extending distally therefrom. Housing 22 is preferably formed from molded housing half-sections 22a and 22b and includes a barrel portion 26 having a longitudinal axis aligned with the longitudinal axis of body portion 24 and a stationary handle portion 28 extending obliquely from barrel portion 26. Ultrasonic transducer 30 is supported within and extends from the proximal end of housing 22 and is connected to control module 14 via cable 18. Jaw assembly 32 is disposed adjacent the distal end of elongated body portion 24 and is actuated by moving movable handle 36 with respect to stationary handle portion 28. Movable handle 36 and stationary handle portion 28 include openings 38 and 40, respectively, to facilitate gripping and actuation of ultrasonic instrument 12. Elongated body portion 24 is supported within rotatable knob 34 and may be selectively rotated by rotating knob 34 with respect to housing 22 to change the orientation of jaw assembly 32.

Figure 3:
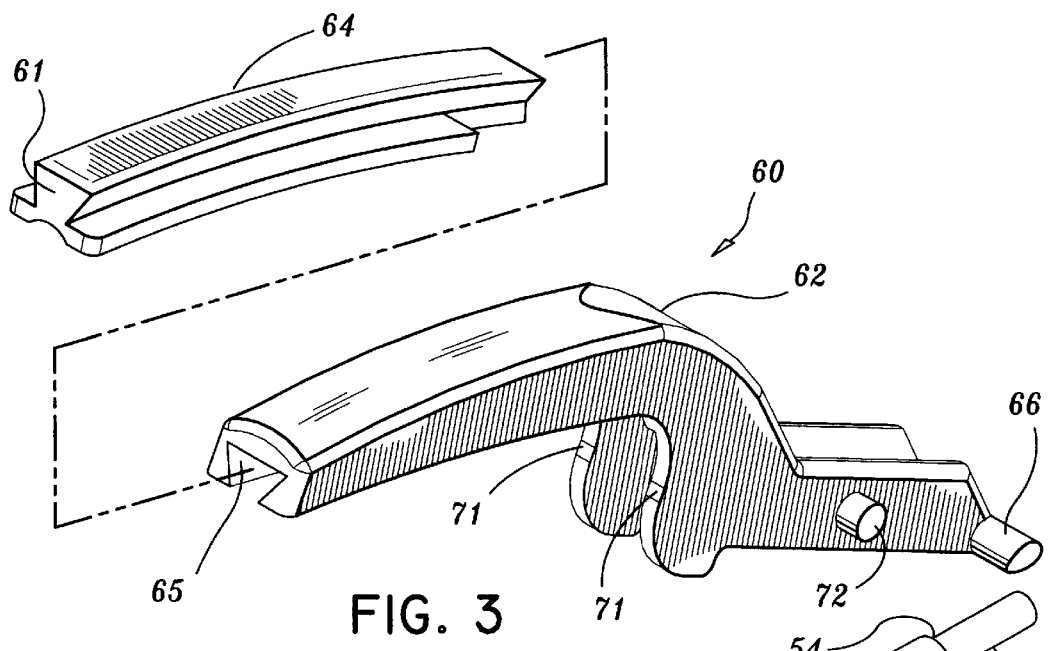
FIG. 3 is a perspective view with parts separated of the clamp of the ultrasonic instrument of FIG. 1.
Figure 4:
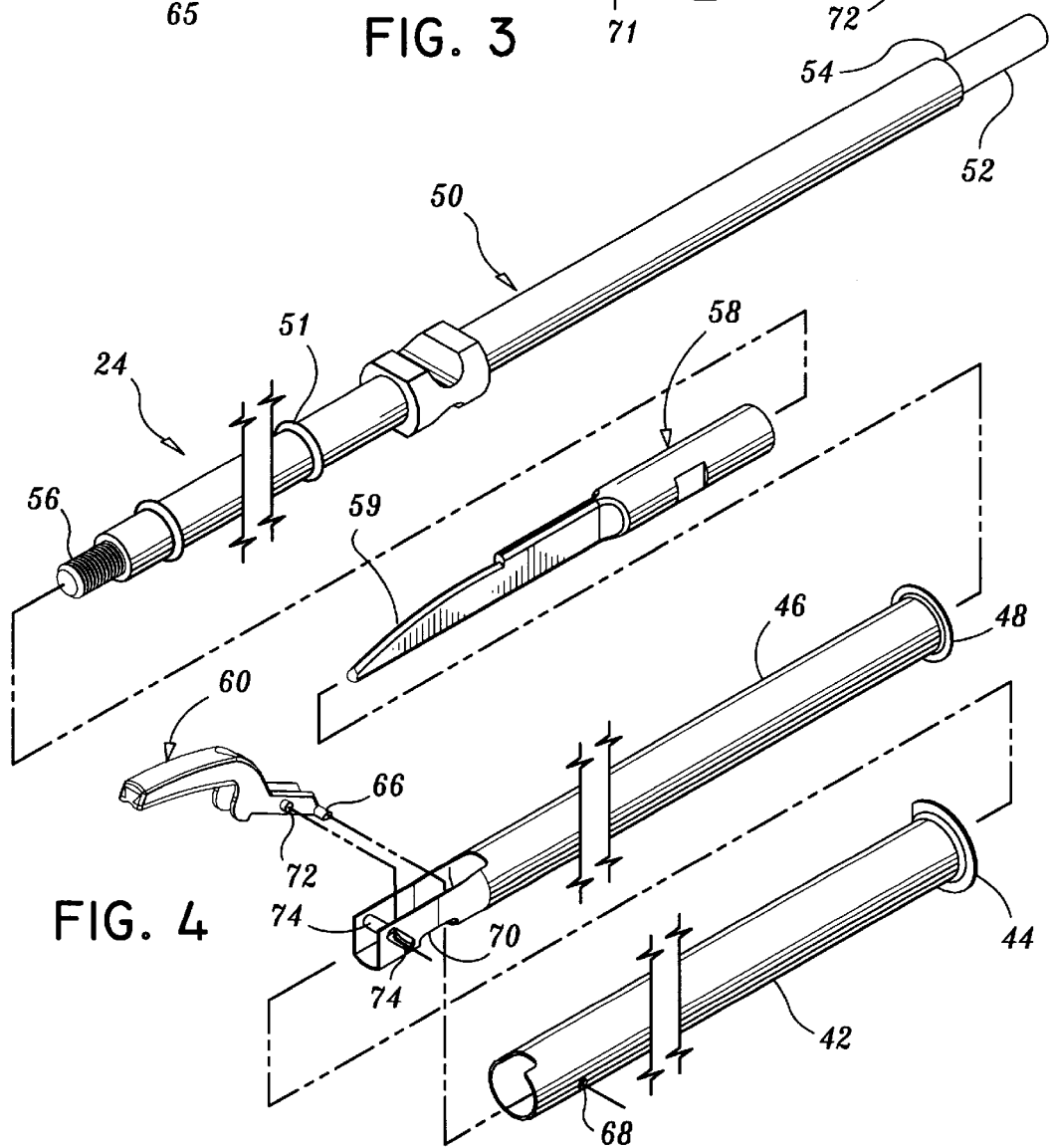
FIG. 4 is a perspective view with parts separated of the elongated body portion of the ultrasonic instrument of FIG. 1.

FIGS. 3 and 4 illustrate elongated body portion 24 with parts separated. Elongated body portion 24 includes an outer tube 42 which is preferably cylindrical and has a proximally located annular flange 44 dimensioned to engage rotatable knob 34 (FIG. 2) as described below. An elongated actuator tube 46, which is also preferably cylindrical, is configured to be slidably received within outer tube 42 and includes a proximally located annular flange 48 dimensioned to engage coupling member 98 (FIG. 5) which is supported within housing 22 (FIG. 2) and will be described in detail below. Vibration coupler 50 is dimensioned to extend through elongated actuator tube 46 and includes a proximal end 52 having a reduced diameter portion 54 configured to operatively engage ultrasonic transducer 30 (FIG. 5) and a distal end 56 adapted to be operatively connected to cutting jaw 58. A plurality of silicon rings 51 can be molded or otherwise attached to the nodal points along vibration coupler 50 to seal between vibration coupler 50 and actuator tube 46. Preferably, cutting jaw 58 includes an internal proximal threaded bore (not shown) which is dimensioned to receive threaded distal end 56 of vibration coupler 50. Alternately, cutting jaw 58 can be formed integrally with vibration coupler 50, cutting jaw 58 may include a threaded proximal end configured to be received within a threaded bore formed in vibration coupler 50, or other attachment devices can be used. A clamp 60 having a clamp body 62 and a tissue contact member 64 removably secured to clamp body 62 is operatively connected to the distal end of actuator tube 46. Clamp body 62 includes a pair of tissue receiving stops 71 that define the proximal end of the exposed blade surface 59. Tissue contact member 64 is preferably composed of teflon and is preferably removably fastened to clamp body 62 by a tongue and groove fastening assembly (reference numerals 61 and 65, respectively), although other fastening assemblies are also envisioned. Tissue contact member 64 functions to isolate clamp 60, which is preferably metallic, from jaw 58 which is also preferably metallic to prevent metal to metal contact. Tissue contact member 50 also functions to grip tissue to prevent movement of the tissue with vibrating cutting jaw 58. Alternately, at least one row of teeth may be positioned on clamp 60 to grip tissue, such as disclosed in U.S. patent application Ser. No. 08/911,207 filed under Express Mail No. EM233327669US, which is incorporated herein by reference. Pivot members (pins) 66 located at the proximal end of clamp body 62 are configured to be received within openings 68 formed in the distal end of outer tube 42. A guide slot 70 formed in the distal end of actuator tube 46 permits relative movement between actuator tube 46 and clamp body 62 by allowing pins 66 to move in guide slot 70. A pair of camming members 72 are also formed on clamp body 62 and are positioned to be received within cam slots 74 formed in the distal end of actuator tube 46. Movement of actuator tube 46 and clamp 60 will be described in detail below.

Figures 7, 8:
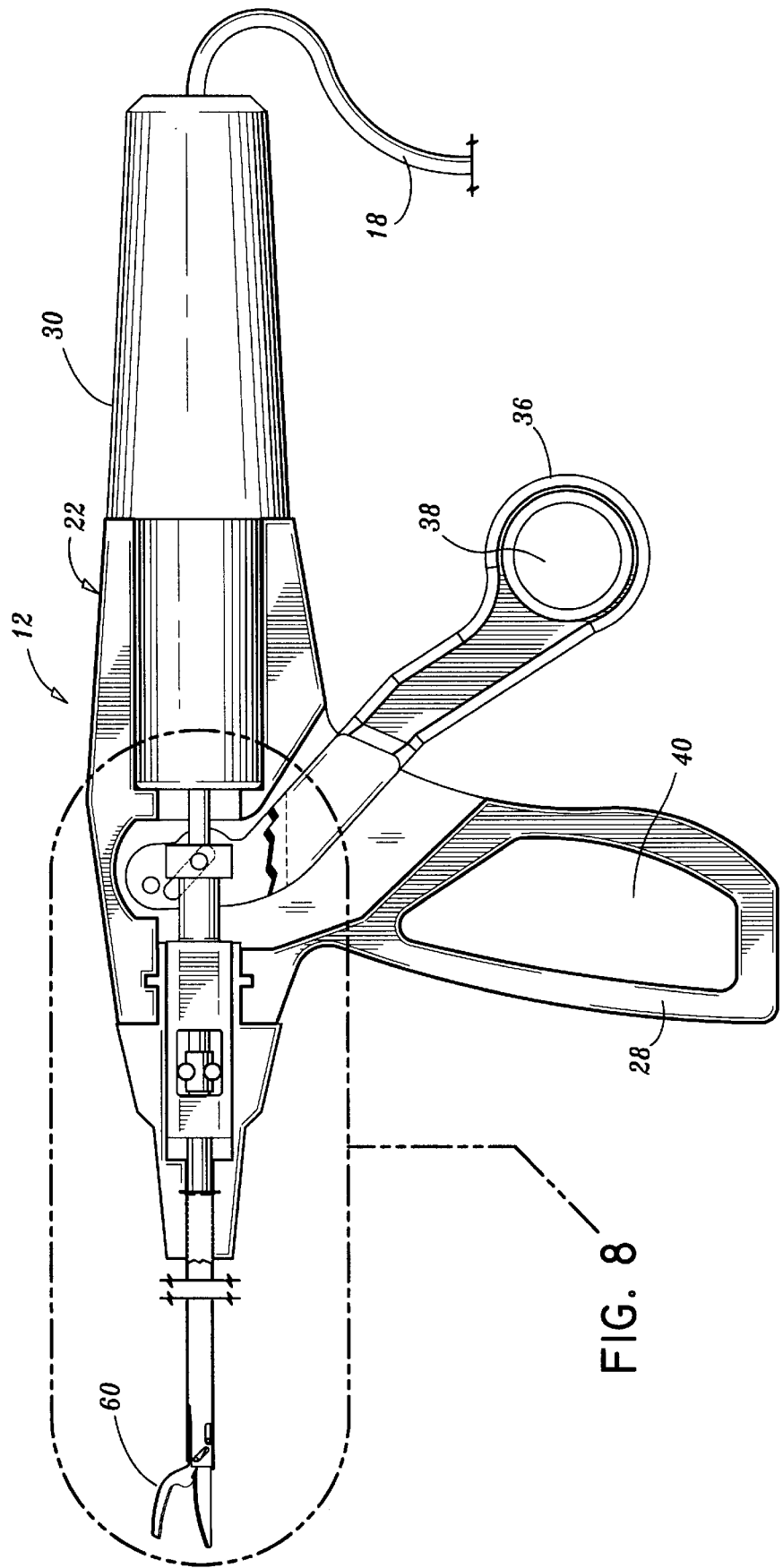
FIG. 7 is a side partial cutaway view of the ultrasonic instrument of FIG. 1 in the open position.
FIG. 8 is an enlarged view of the indicated area of detail of FIG. 7 illustrating the clamp in the open position.
Figures 8, 9, 10:
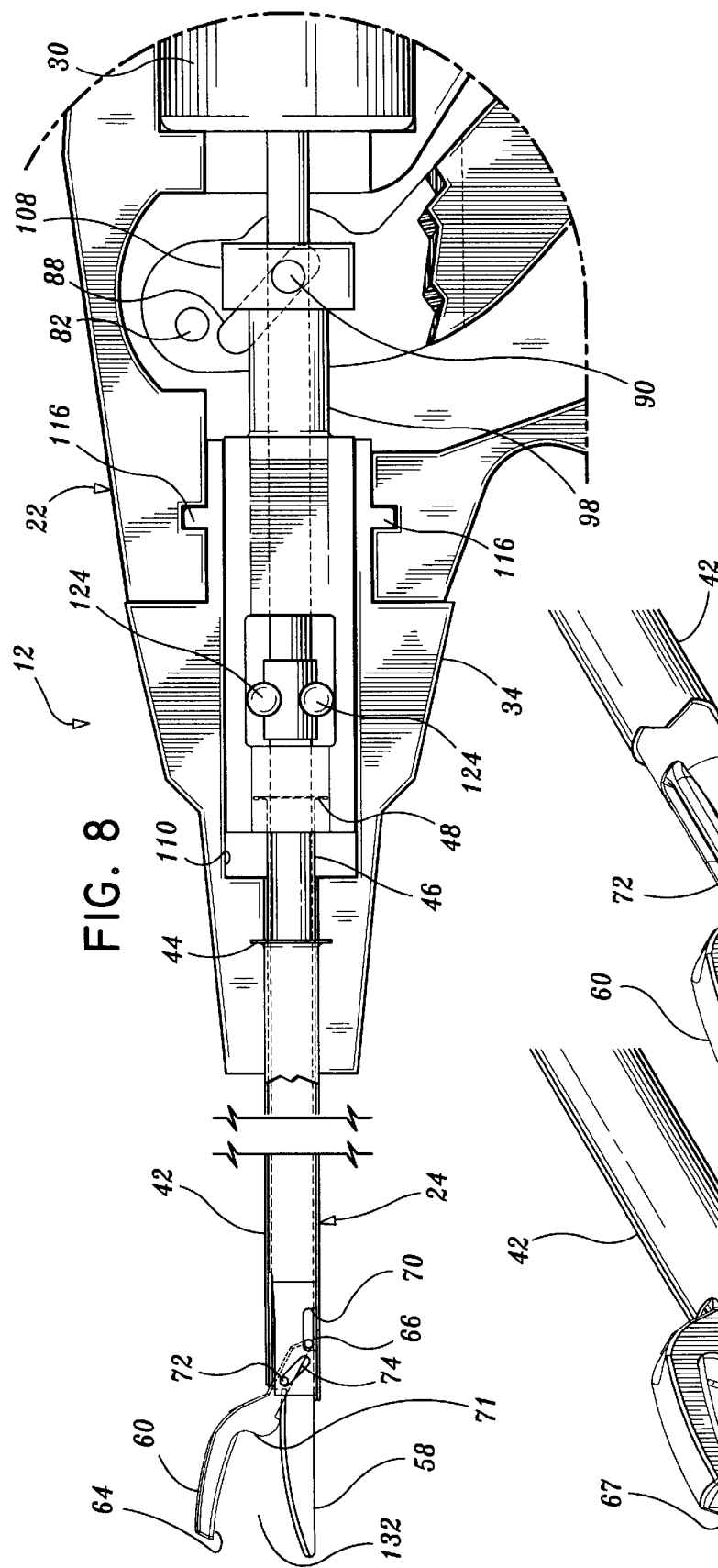
FIG. 9 is a perspective view of the distal end of the elongated body portion of the ultrasonic instrument of FIG. 1 with the clamp in the open position.
FIG. 10 is a perspective partial cutaway view of the distal end of the elongated body portion of the ultrasonic instrument of FIG. 1 with the clamp in the open position.

Cutting jaw 58 includes a curved blade surface 59 that slopes downwardly and outwardly in the distal direction. Preferably, the entire blade surface 59 exposed to tissue, i.e., the portion of blade surface 59 between tissue receiving stops 71 and the distal end of blade surface 59, has a tangent which defines an angle with respect to the longitudinal axis of elongated body portion 24 that varies along the length of blade surface 59 from about 5 degrees to about 75 degrees. Ideally, the angle defined by a line tangent to the blade surface and the longitudinal axis of elongated body portion 24 varies from about 5 degrees to about 45 degrees along the length of the blade surface. The curved blade surface provides better visibility at the surgical site. Clamp 60 is movable from an open position in which tissue contact member 64 is spaced apart from blade surface 59 (FIGS. 7 and 8) to a clamped position in which tissue contact member is in juxtaposed close alignment with blade surface 59 (FIGS. 11–13) to clamp tissue therebetween. The interior surface of tissue contact member 64 is curved to correspond to blade surface 59. In the clamped position, note the positioning of tissue contact member 64 with respect to blade surface 59. Actuation of clamp 60 from the open position to the clamped position will be described in detail below.

Figure 5:
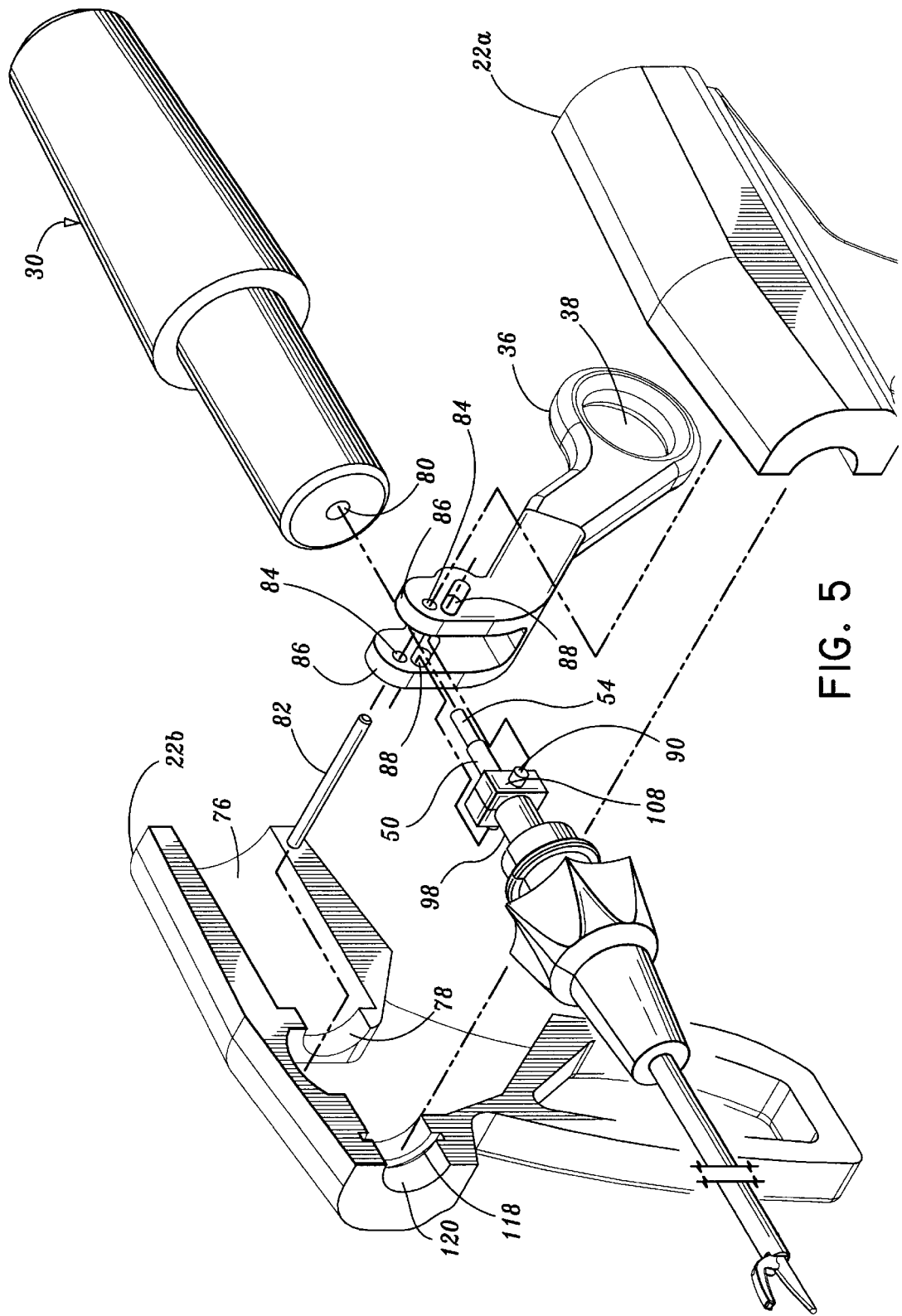
FIG. 5 is a perspective view with parts separated of the ultrasonic instrument of FIG. 1.
Figure 6:
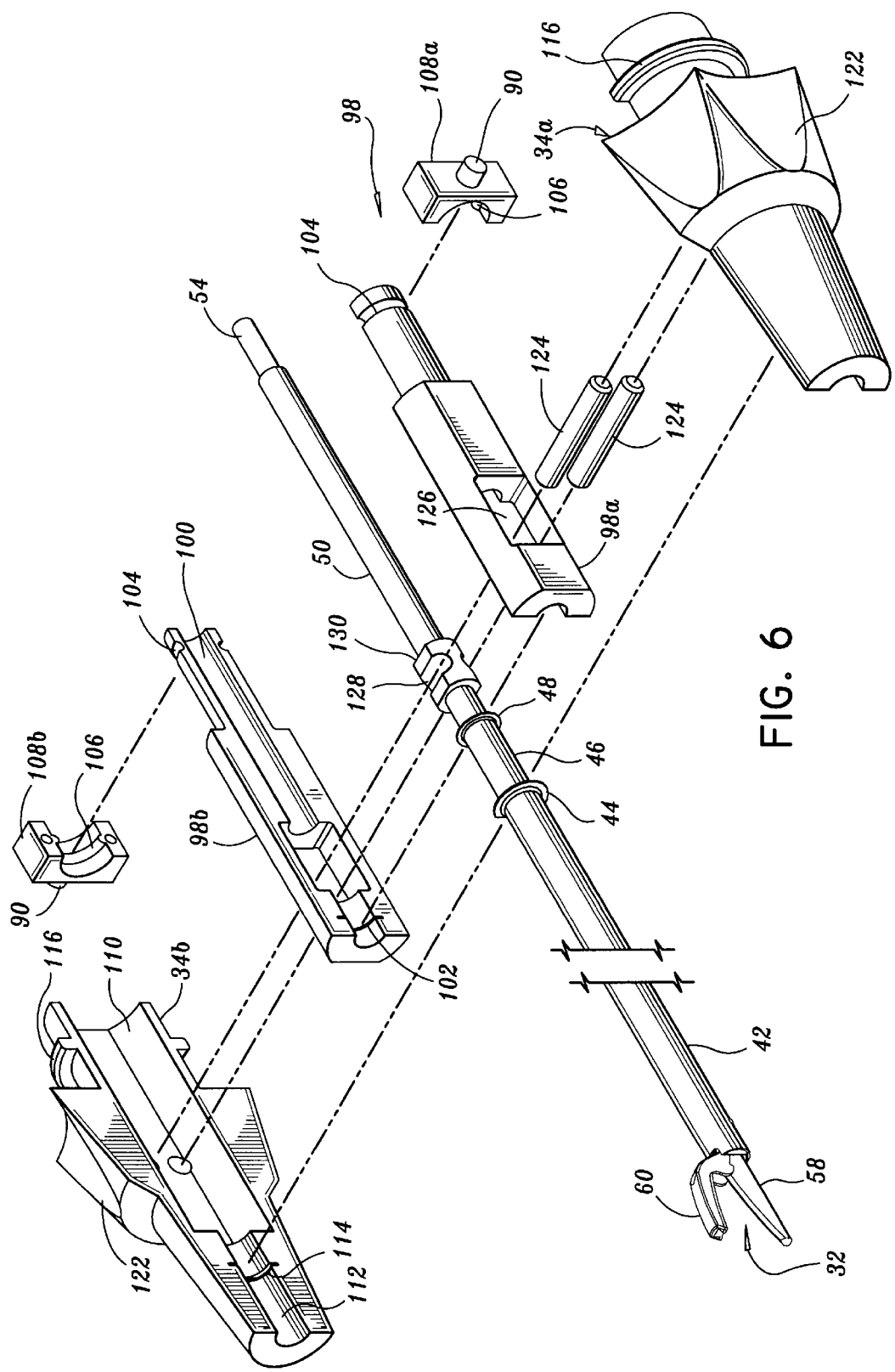
FIG. 6 is a perspective view with parts separated of the rotation assembly of the ultrasonic instrument of FIG. 1.

Referring now to FIGS. 5 and 6, the handle assembly and the rotation assembly will now be discussed. Housing half-sections 22a and 22b define a chamber 76 configured to receive a portion of ultrasonic transducer 30. Chamber 76 has an opening 78 communicating with the interior of housing 22. Ultrasonic transducer 30 includes a bore 80 configured to receive proximal end 54 of vibration coupler 50. In the assembled condition, proximal end 54 extends through opening 78 into bore 80. Ultrasonic transducer 30 may be secured within housing 22 to vibration coupler 50 using any known attachment apparatus. Preferably, a torque wrench, such as disclosed in copending U.S. patent application Ser. No. 08/911,207 incorporated above, can be used to secure ultrasonic transducer 30 to vibration coupler 50. As disclosed therein, the proximal end of transducer 30 may be configured to engage the torque wrench. Movable handle 36 is pivotally connected between housing half-sections 22a and 22b about pivot pin 82 which extends through holes 84 formed in legs 86 of movable handle 36. A cam slot 88 formed in each leg 86 is configured to receive a protrusion 90 projecting outwardly from coupling member 98 (FIG. 6).

As illustrated in FIG. 6, coupling member 98 operatively connects movable handle 36 to actuator tube 46 and is preferably formed from molded half-sections 98a and 98b to define a throughbore 100 dimensioned to slidably receive the proximal end of vibration coupler 50. Coupling member 98 has an inner distally located annular groove 102 dimensioned to receive annular flange 48 of actuator tube 46 and an outer proximally located annular groove 104. Groove 104 is positioned to receive an annular rib 106 formed on the internal wall of a swivel member 108 (FIG. 5). Swivel member 108 is preferably formed from molded half-sections 108a and 108b and permits rotation of coupling member 98 relative to movable handle 36. Protrusions 90 project outwardly from sidewalls of swivel member 108 and extend through cam slots 88 of movable handle 36 (FIG. 5).

Referring to FIGS. 5 and 6, rotation knob 34 is preferably formed from molded half-sections 34a and 34b and includes a proximal cavity 110 for slidably supporting coupling member 98 and a distal bore 112 dimensioned to receive outer tube 42. An annular groove 114 formed in bore 112 is positioned to receive annular flange 44 of outer tube 42. The outer wall of knob 34 has a proximally located annular ring 116 dimensioned to be rotatably received within annular slot 118 formed in opening 120 of housing 22. The outer wall of knob 34 also includes scalloped surface 122 to facilitate gripping of rotatable knob 34. Annular ring 116 permits rotation of knob 34 with respect to housing 22 while preventing axial movement with respect thereto. A pair of cylindrical rods 124 extend between half-sections 34a and 34b through a rectangular opening 126 formed in coupling member 98. Rods 124 engage a pair of concave recesses 128 formed in fitting 130 which is fastened about vibration coupler 50, such that rotation of knob 34 causes rotation of vibration coupler 50 and thus rotation of blade 58 and clamp 60. Alternately, recesses 128 can be monolithically formed with vibration coupler 50.

FIGS. 7–10 illustrate ultrasonic instrument 12 with clamp 60 in the open position. The elongated body 24 which includes clamp 60 and blade 58, and housing 22 which includes handles 28 and 36, are packaged as an integral unit, e.g., non-detachably connected, that requires no assembly by the user prior to use. That is, the user needs only to attach transducer 30 to housing 22 to ready instrument 12 for use. In the open position, movable handle 36 is spaced rearwardly from stationary handle portion 28 and protrusions 90 are positioned in the lower proximal portion of cam slots 88. At the distal end of ultrasonic instrument 12, pivot members 66 are positioned near the distal end of guide slots 70 and camming members 72 are positioned in the upper distal portion of cam slots 74. Tissue contact member 64 of clamp 60 is spaced from blade surface 59 to define a tissue receiving area 132. The proximal end of tissue receiving area 132 is defined by tissue receiving stops 71 which are preferably integrally formed with clamp body 62 and extend below blade surface 59. Preferably, the distal end of blade 58 is rounded to prevent inadvertent damage to tissue during use of instrument 12 and tissue contact surface 64 is also preferably formed with a longitudinally extending concavity 67 to receive tissue therein. Alternately, the distal end of blade 58 may be formed in any shape which may be suitable to a particular surgical application, i.e., pointed, flat, etc. Moreover, tissue contact surface 64 need not be formed with a concavity but may be flat, angled, etc.

Figure 11:
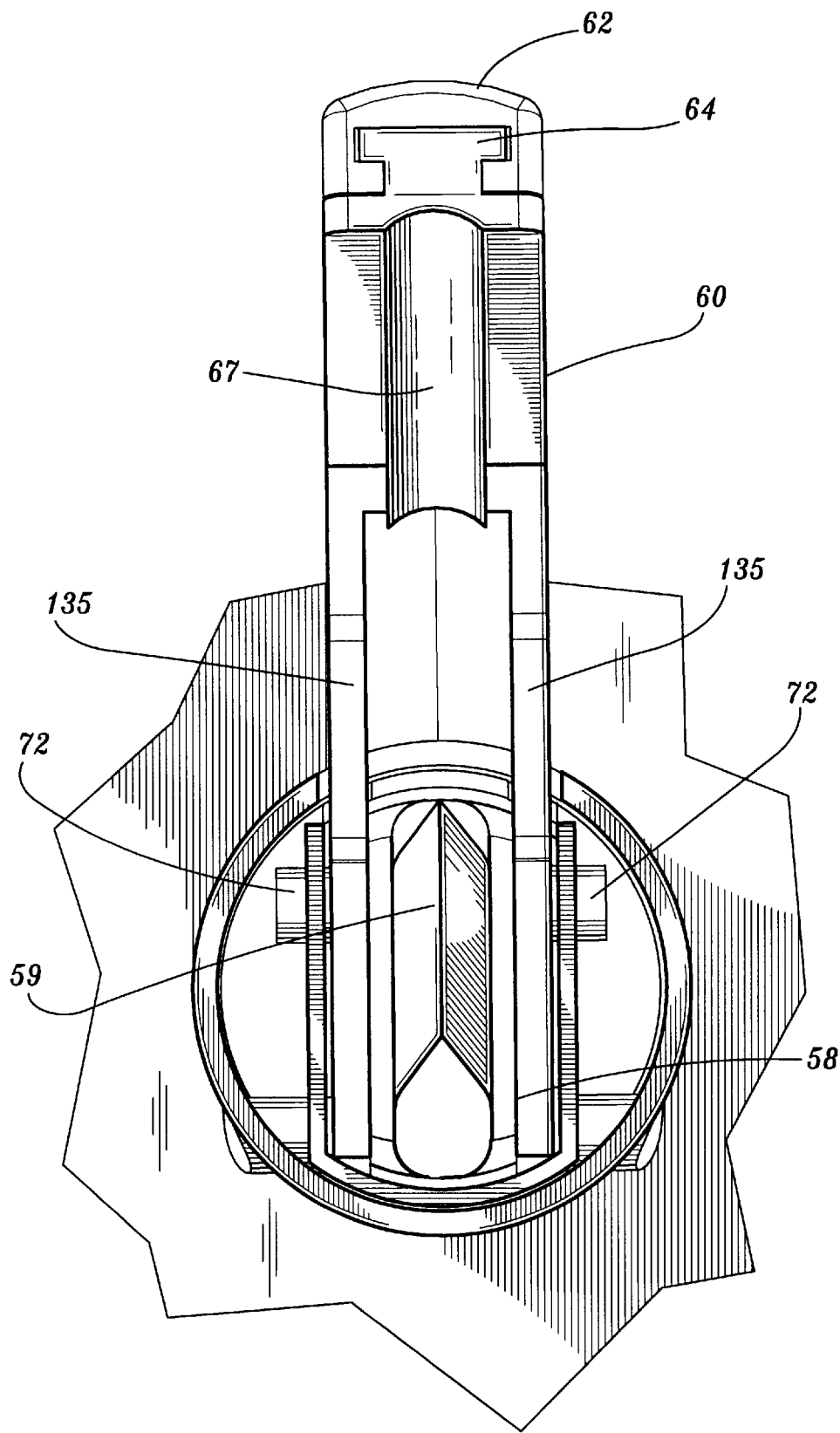
FIG. 11 is a front elevational view of the ultrasonic instrument of FIG. 1.
Figure 12:
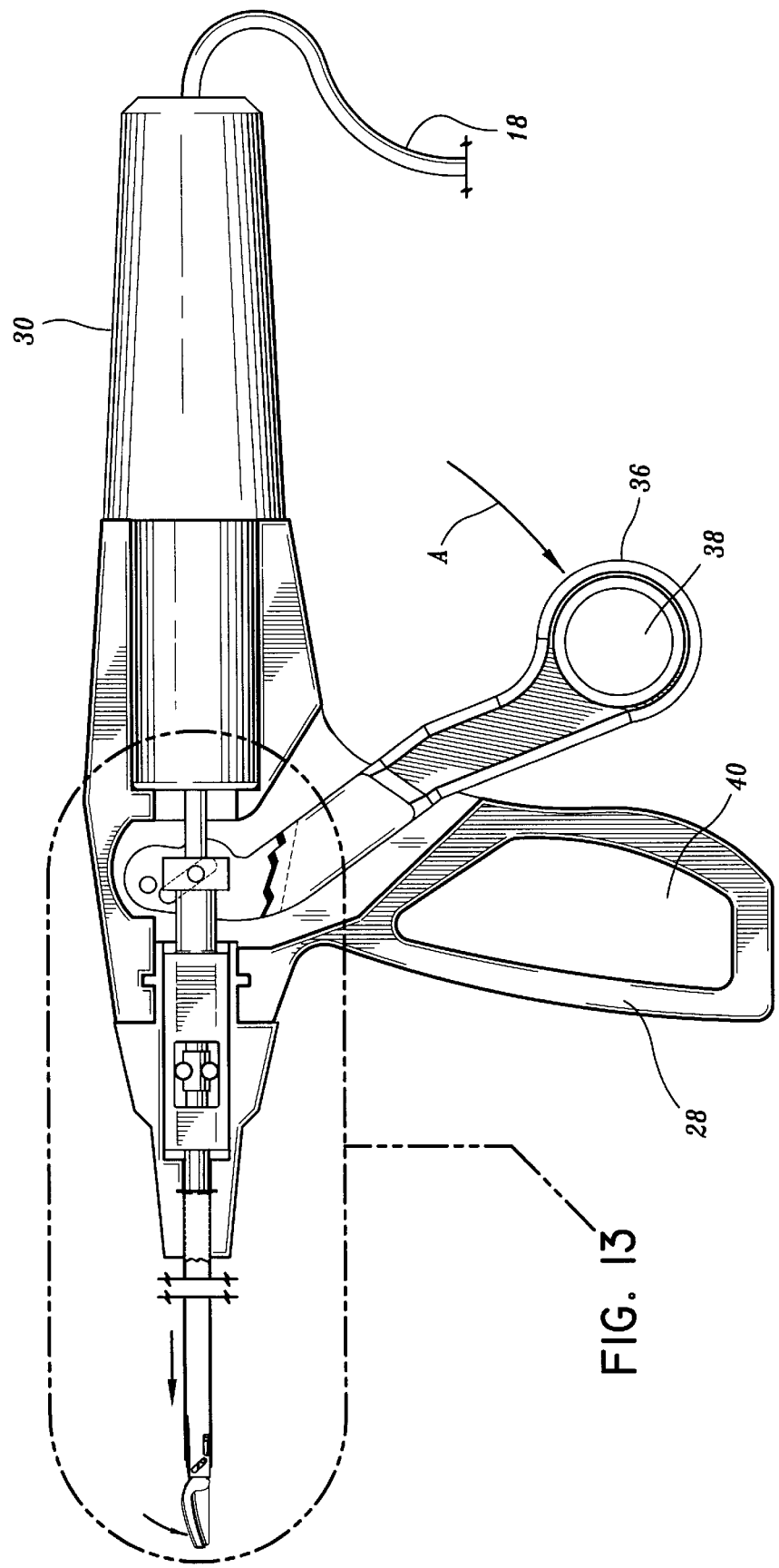
FIG. 12 is a side partial cutaway view of the ultrasonic instrument of FIG. 1 with the clamp in the clamped (closed) position.

Referring to FIGS. 11–15, when movable handle 36 is pivoted clockwise about pivot member 82 towards stationary handle portion 28, in the direction indicated by arrow "A" in FIG. 11, cam slot 88 engages protrusion 90 of swivel member 108 to advance coupling member 98 distally within cavity 110 of rotation knob 34. Since actuator tube 46 is attached to coupling member 98 by an annular flange 48, actuator tube 46 is also advanced distally in the direction indicated by arrow "B" in FIG. 12. Movement of actuator tube 46 distally causes cam slots 74 to move into engagement with camming members 72 to pivot clamp body 62 about pivot members 66, in the direction indicated by arrow "C" in FIG. 13, to move clamp member 62 and tissue contact member 64 into the clamped position. In the clamped position, protrusions 90 are located in a central portion of cam slots 88, pivot members 66 are located near the proximal end of guide slots 70, and camming members 72 are located in the proximal lower portion of cam slots 74.

Figure 15:
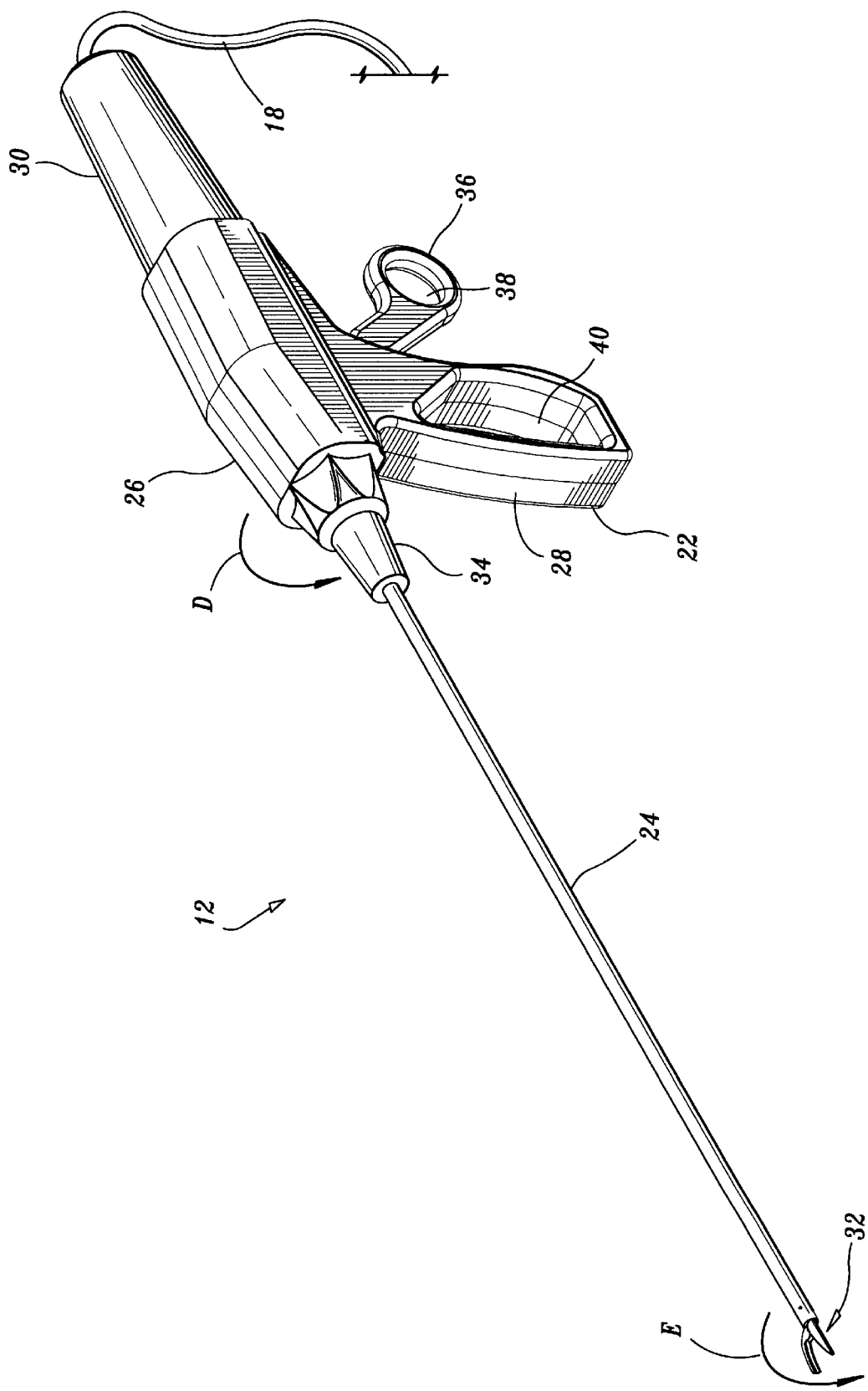
FIG. 15 is a perspective view of the ultrasonic instrument of FIG. 1 with the elongated body portion partially rotated.

Elongated body portion 24 can be freely rotated with respect to housing 22 by rotating rotation knob 34. As illustrated in FIG. 15, rotation of knob 34 in the direction indicated by arrow "D" causes rotation of jaw assembly 32 in the direction indicated by arrow "E". Knob 34 is positioned adjacent housing 22 to facilitate one handed operation of both movable handle 36 and rotation knob 34.

Referring again to FIG. 1, elongated body portion 24 is dimensioned to extend through a trocar assembly 140, and is preferably dimensioned to extend through a 5 mm trocar assembly. During use, elongated body portion 24 is slid through trocar assembly 140 with jaw assembly 32 in the clamped or closed position to a position adjacent tissue (not shown) to be dissected and/or coagulated. An optical unit (not shown) can also be positioned adjacent the surgical site to facilitate viewing of the procedure. Jaw assembly 32 is opened and tissue to be dissected and/or coagulated is positioned within tissue receiving area 132 (See also FIG. 9). Tissue receiving stops 71 prevent tissue from moving past the proximal end of blade surface 59. Next, jaw assembly 32 is closed to clamp tissue between tissue contact member 64 and blade surface 59. Power is supplied to ultrasonic instrument 12 via control module 14 to initiate vibration of blade 58 to effect dissection and/or coagulation of tissue. Because of the curve of blade surface 59, the force applied by blade surface 59 to the tissue being dissected can be selectively increased or decreased as instrument 12 is moved forward through trocar assembly 140 by adjusting the location of the tissue on blade surface 59 and thus changing the angle of the force applied to the tissue being dissected.

Figure 16A:
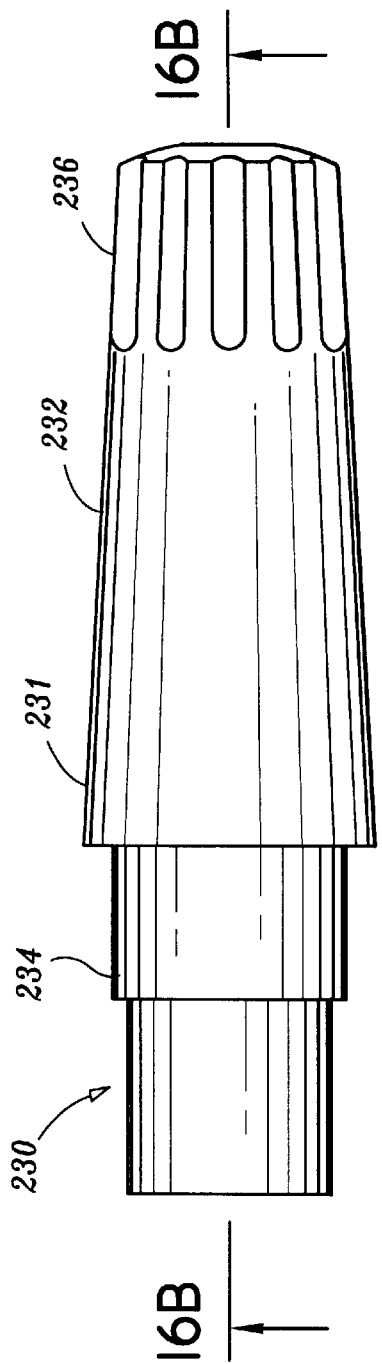
FIG. 16A is a side view of an alternate embodiment of the ultrasonic transducer of FIG. 1.
Figure 16B:
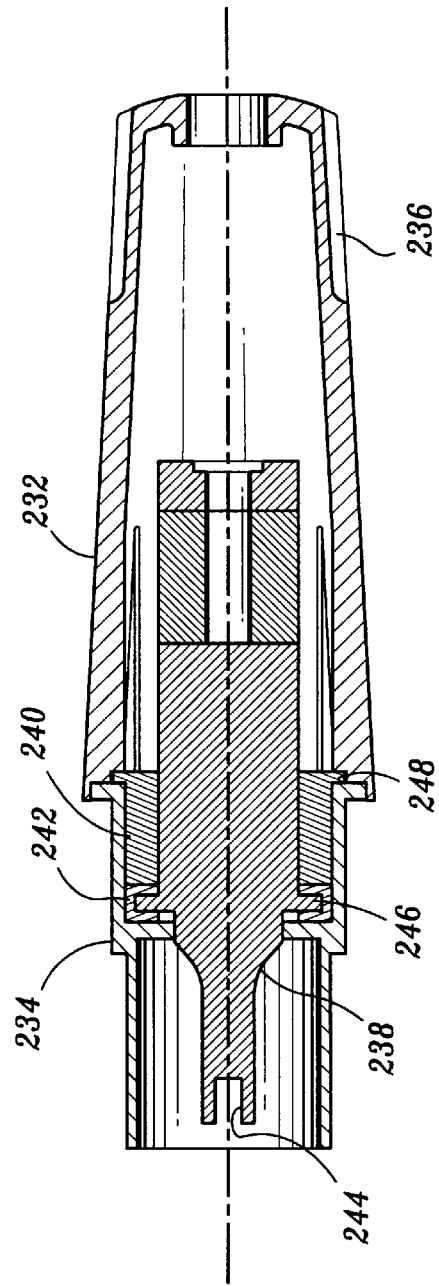
FIG. 16B is a side cross-sectional view taken along section line 16B—16B of FIG. 16B.
Figure 16C:
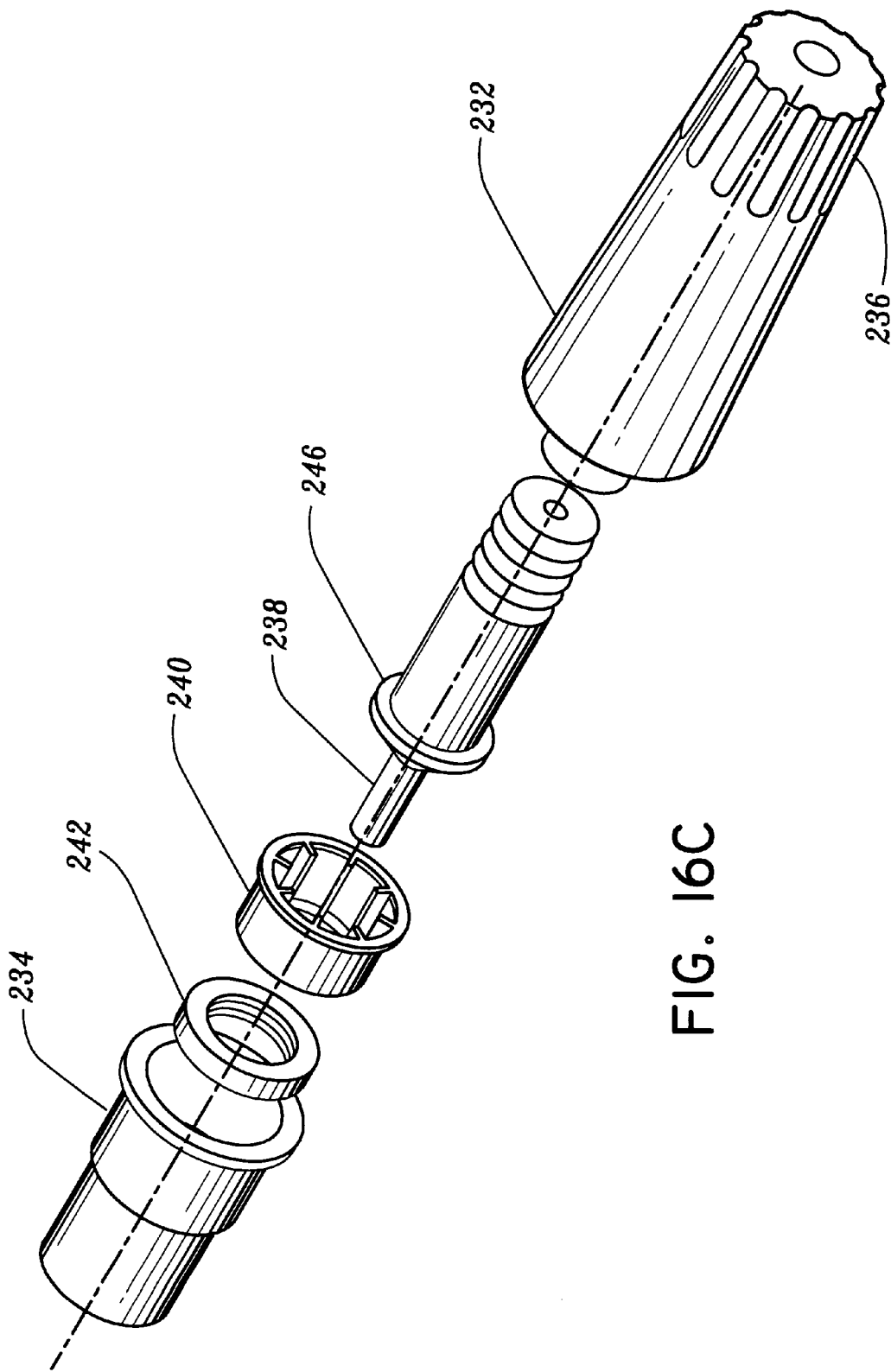
FIG. 16C is a perspective view with parts separated of the ultrasonic transducer of FIG. 16A.

FIGS. 16A–16C illustrate an alternate embodiment of the ultrasonic transducer shown generally as 230. Ultrasonic transducer 230 includes a housing 231 having a proximal housing portion 232 and a distal housing portion 234. Proximal housing portion 232 has a scalloped section 236 adjacent its proximal end. Transducer horn 238 is supported within housing 231 by support collar 240 and annular ring 242. The distal end of transducer horn 238 includes a threaded bore 244 dimensioned to engage reduced diameter portion 54 of vibration coupler 50 (FIG. 4). As best illustrated in FIG. 16B, transducer horn 238 is formed with annular flange 246, about which annular ring 242 is received. The proximal end of support collar 240 also includes an annular flange 248 which, in an assembled condition, is clamped between proximal and distal housing portions 232 and 234 to fixedly retain support collar 240 in position within housing 231. The distal end of support collar 240 engages annular ring 242 to retain annular ring 242 and thus horn 238 in a longitudinally fixed position within housing 231.

Figure 17A:
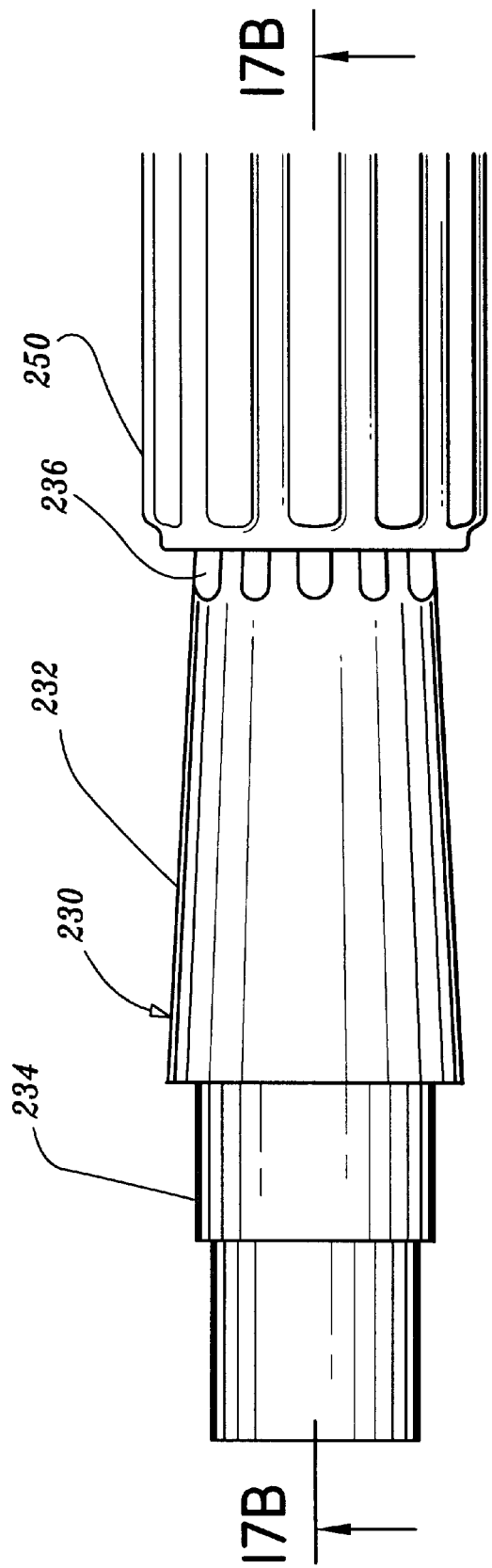
FIG. 17A is a side view of a torque wrench assembly in engagement with the ultrasonic transducer of FIG. 16A.
Figure 17B:
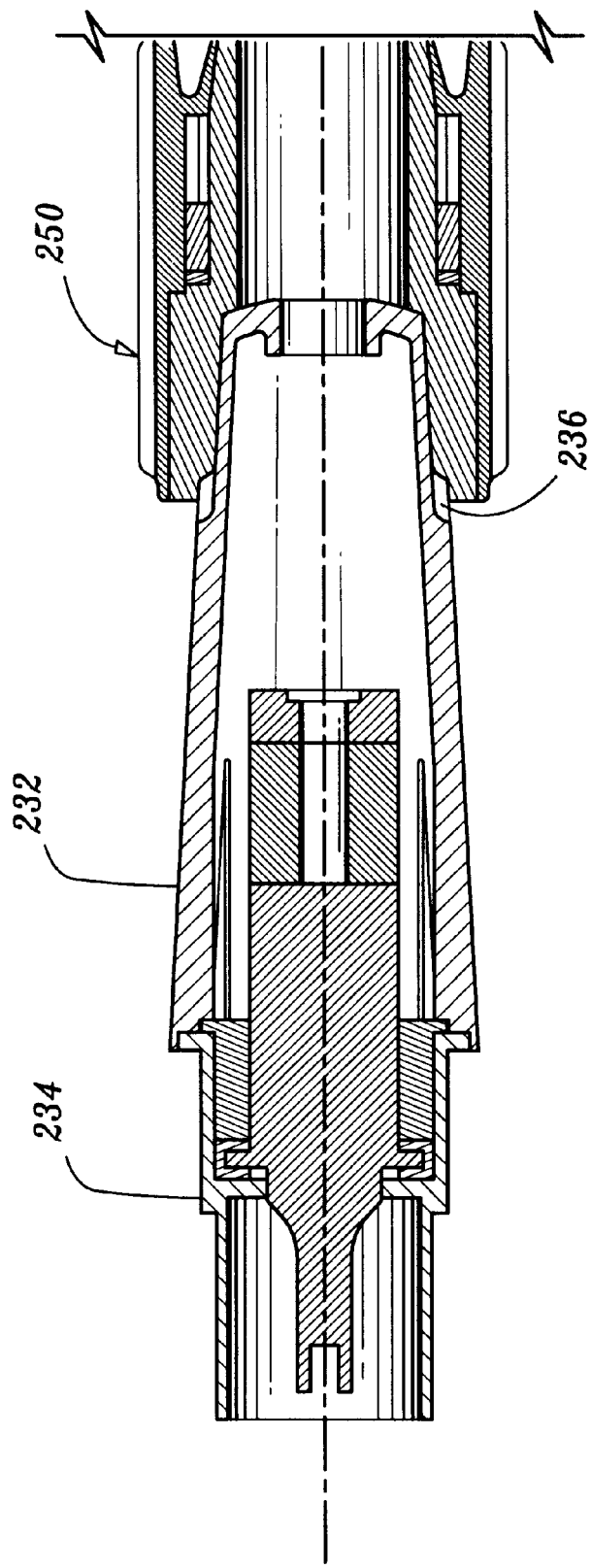
FIG. 17B is a side cross-sectional view taken along section line 17B—17B of FIG. 17A.

Referring to FIGS. 17A–17B, torque wrench assembly 250 is configured and dimensioned to engage scalloped section 236 of ultrasonic transducer 230 to facilitate assembly of transducer assembly 230 with the remaining portion of ultrasonic instrument 12. Torque wrench assembly 250 assures that horn 238 and vibration coupler 50 (FIG. 4) are properly connected, i.e., properly torqued.

It will be understood that various modifications may be made to the embodiments herein. For example, vibration coupler 50 and blade 58 may be monolithically formed or attached using structure other than screw threads. Different actuator assemblies other than the actuator tube having a camming surface can be used to pivot the clamp member to the clamped position. Further, the elongated body portion of the instrument can be dimensioned to extend through other than 5 mm trocar assemblies, e.g., 10 mm, 12 mm, etc. Therefore, the above description should not be construed as limiting, but merely as exemplifications of preferred embodiments. Those skilled in the art will envision other modifications within the scope and spirit of the claims appended hereto.

What is claimed is:

1. An ultrasonic instrument comprising:
   a) a vibration coupler adapted to be operably connected to an ultrasonic generator and having a longitudinal axis; and
   b) a cutting jaw extending from a distal end portion of the vibration coupler and having a longitudinal axis substantially aligned with the longitudinal axis of the vibration coupler, the cutting jaw having a curved blade surface that slopes downwardly and outwardly towards the distal end of the cutting jaw, wherein the curved blade surface is convex.

2. An ultrasonic instrument according to claim 1, further including a clamp member having a tissue engaging surface, the clamp member being movable from an open position in which the tissue engaging surface is spaced from the blade surface to a clamped position in which the clamp member is in juxtaposed alignment with the cutting jaw to capture tissue between the tissue engaging surface and the blade surface.

3. An ultrasonic instrument according to claim 2, wherein the tissue contact surface is removably fastened to the clamp member.

4. An ultrasonic instrument according to claim 2, wherein the clamp member is pivoted from the open to the clamped position.

5. An ultrasonic instrument according to claim 4, further comprising a handle assembly and an actuator member operatively connected to the handle assembly and to the clamp member, the handle assembly being movable to move the clamp member from the open position to the clamped position.

6. An ultrasonic instrument comprising:
   a) a vibration coupler adapted to be operably connected to an ultrasonic generator and having a longitudinal axis;
   b) a cutting jaw extending from a distal end portion of the vibration coupler and having a longitudinal axis substantially aligned with the longitudinal axis of the vibration coupler, the cutting jaw having a curved blade surface that slopes downwardly and outwardly towards the distal end of the cutting jaw;
   c) a clamp member having a tissue engaging surface, the clamp member being pivotable from an open position in which the tissue engaging surface is spaced from the blade surface to a clamped position in which the clamp member is in juxtaposed alignment with the cutting jaw to capture tissue between the tissue engaging surface and the blade surface; and
   d) a handle assembly and an actuator member operatively connected to the handle assembly and to the clamp member, the handle assembly being movable to facilitate movement of the clamp member from the open position to the clamped position, wherein the clamp member includes a camming member positioned in a cam slot formed in the actuator member, the cam slot being movable relative to the camming member to pivot the clamp member between the open position and the clamped position.

7. An ultrasonic instrument according to claim 2, wherein the clamp member and cutting jaw are non-detachably connected to each other and require no assembly prior to use.

8. An ultrasonic instrument according to claim 1, wherein the blade surface is curved such that the angle defined by a line drawn tangent to the blade surface and the longitudinal axis of the vibration coupler varies from about 5 degrees to about 75 degrees along the blade surface.

9. An ultrasonic instrument according to claim 8, wherein the angle varies from about 5 degrees to about 45 degrees.

10. An ultrasonic instrument according to claim 1, further comprising a rotatable collar operatively associated with the vibration coupler, the clamp member, and the cutting jaw such that rotation of the rotatable collar causes corresponding rotation of the vibration coupler, the clamp member and the cutting jaw about the longitudinal axis of the vibration coupler.

11. An ultrasonic instrument comprising:
    a) a handle assembly;
    b) an elongated body portion extending distally from the handle assembly, the elongated body portion including,
       1) an outer tubular member;
       2) a vibration coupler adapted to be operatively connected to an ultrasonic generator, the vibration coupler being positioned within the outer tubular member; and
       3) a cutting jaw operatively associated with the vibration coupler, the cutting jaw having a curved blade surface that slopes downwardly and outwardly toward the distal end of the cutting jaw, wherein the curved blade surface is convex.

12. An ultrasonic instrument according to claim 11, wherein the blade surface is curved such that the angle defined by a line drawn tangent to the blade surface and the longitudinal axis of the elongated body portion varies along the length of the blade surface from about 5 degrees to about 75 degrees.

13. An ultrasonic instrument according to claim 12, wherein the angle varies from about 5 degrees to about 45 degrees.

14. An ultrasonic instrument according to claim 11, wherein the elongated body portion further comprises a clamp member positioned adjacent the cutting jaw, the clamp member having a tissue contact surface movable from an open position spaced from the blade surface to a clamped position in juxtaposed alignment with the blade surface to clamp tissue therebetween.

15. An ultrasonic instrument according to claim 14, wherein in the open position the clamp member and the cutting jaw define a tissue receiving area, the clamp member having a tissue engaging stop that defines the proximal end of the tissue receiving area and the proximal end of the blade surface.

16. An ultrasonic instrument according to claim 15, wherein the handle assembly includes a handle movable between first and second positions, the movable handle being operatively associated with the clamp member to move the clamp member between the open and clamped positions as the movable handle is moved between the first and second positions.

17. An ultrasonic instrument according to claim 15, further comprising a tubular actuator member having a proximal end operatively connected to the movable handle and a distal end operatively connected to the clamp member.

18. An ultrasonic instrument according to claim 14, wherein the vibration coupler, cutting jaw and clamp member are non-detachably connected together and require no assembly prior to use.

19. An ultrasonic instrument according to claim 14, wherein the blade surface is curved such that the angle defined by a line drawn tangent to the blade surface and the longitudinal axis of the elongated body portion varies along the length of the blade surface from about 5 degrees to about 75 degrees.

20. An ultrasonic instrument according to claim 11, wherein the elongated body portion is dimensioned to be received within a 5 mm trocar assembly.

* * * * *